United States Patent
Slaaby et al.

(10) Patent No.: US 9,120,871 B2
(45) Date of Patent: Sep. 1, 2015

(54) PROCESS FOR PREPARING FGF21 WITH LOW DEGREE OF O-GLYCOSYLATION

(75) Inventors: Rita Slaaby, Lyngby (DK); Inger Lautrup-Larsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 36 days.

(21) Appl. No.: 13/522,804

(22) PCT Filed: Jan. 20, 2011

(86) PCT No.: PCT/EP2011/050718
§ 371 (c)(1),
(2), (4) Date: Sep. 17, 2012

(87) PCT Pub. No.: WO2011/089170
PCT Pub. Date: Jul. 28, 2011

(65) Prior Publication Data
US 2013/0005951 A1   Jan. 3, 2013

Related U.S. Application Data

(63) Continuation-in-part of application No. 12/692,227, filed on Jan. 22, 2010.

(60) Provisional application No. 61/356,086, filed on Jun. 18, 2010, provisional application No. 61/151,355, filed on Feb. 10, 2009, provisional application No. 61/151,357, filed on Feb. 10, 2009, provisional application No. 61/225,387, filed on Jul. 14, 2009.

(30) Foreign Application Priority Data

| | | |
|---|---|---|
| Jan. 23, 2009 | (EP) | 09151227 |
| Feb. 5, 2009 | (EP) | 09152144 |
| Jul. 8, 2009 | (EP) | 09164904 |
| Jan. 22, 2010 | (WO) | PCT/EP2010/050720 |
| Jun. 15, 2010 | (EP) | 10165927 |

(51) Int. Cl.
*C12N 1/19* (2006.01)
*C07K 14/50* (2006.01)
*A61K 38/00* (2006.01)

(52) U.S. Cl.
CPC *C07K 14/50* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,714,377 A | 2/1998 | Tanner et al. | |
| 7,262,287 B2 * | 8/2007 | Kang et al. | 536/23.2 |
| 2002/0068325 A1 | 6/2002 | Ng et al. | |

FOREIGN PATENT DOCUMENTS

| | | |
|---|---|---|
| WO | 2006/028595 A2 | 3/2006 |
| WO | 2006/136831 A2 | 12/2006 |
| WO | 2009/105357 A1 | 8/2009 |
| WO | 2010/084169 A2 | 7/2010 |

OTHER PUBLICATIONS

Takamatsu Shinji, et al, Glycoconjugate Journal, "Monitoring O the Tissue Distribution of Fibroplast Growth Factor Containing a High Mannose-Type Sugar Chain Produced in Mutant Yeast", 2004, vol. 20, No. 6, pp. 385-397.

Gentzsch, Martina & Tanner, Widmar, The PMT Gene Family: Protein O-Glycosylation in *Saccharomyces cerevisiae* is Vital, The EMBO Journal, vol. 15(21), pp. 5752-5759, 1996.

\* cited by examiner

*Primary Examiner* — Christine J Saoud
(74) *Attorney, Agent, or Firm* — Nonna G. Akopyan

(57) ABSTRACT

Expression of FGF21 in a *S. cerevisiae* pmt2 knock out strain reduces the O-glycosylation significantly and does not decrease the expression level. Expression in mkc7 knock out strain can decrease degradation of FGF21 and analogues thereof. Point mutations at position R17 and R36 can decrease degradation of FGF21 and analogues thereof when they are expressed in yeast.

16 Claims, No Drawings

PROCESS FOR PREPARING FGF21 WITH LOW DEGREE OF O-GLYCOSYLATION

CROSS-REFERENCE TO RELATED APPLICATIONS

This application is a 35 U.S.C. §371 national stage application of International Patent Application PCT/EP2011/050718 (published as WO2011/089170A3), filed Jan. 20, 2011, which claimed priority of International Patent Application PCT/EP2010/050720, filed Jan. 22, 2010, U.S. patent application Ser. No. 12/692,227, filed on Jan. 22, 2010 and European Patent Application EP10165927.4, filed on Jun. 15, 2010; this application further claims priority under 35 U.S.C. §119 of U.S. Provisional Application 61/356,086, filed Jun. 18, 2010.

FIELD OF THIS INVENTION

This invention relates to a special process for preparing Fibroblast Growth Factor 21 (FGF21) and analogues thereof and aspects closely related thereto.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jul. 17, 2012. The Sequence Listing is made up of 2.22 kilobytes, and the information in the specification as originally filed. No new matter is added.

BACKGROUND OF THIS INVENTION

Fibroblast growth factors are polypeptides expressed in developing and adult tissues. They are involved in several physiological mechanisms including for example metabolic regulation and cellular differentiation. A whole family of more than twenty fibroblast growth factors exists (the FGF family). Three members of the FGF family including FGF19, FGF21, and FGF23 form a subfamily functioning as endocrine factors involved in metabolic regulation.

Fibroblast Growth Factor 21 or FGF-21, herein for short FGF21, is expressed preferentially in the liver and has been shown to exert hormone-like metabolic effects.

In decades, it has been possible to prepare a large range of peptides and proteins recombinantly, for example in a bacterium such as *Eschericia Coli* or in yeast such as *Saccharomyces cerevisiae*. Proteins expressed in yeast are often O-glycosylated. In pharmaceutical proteins, O-glycosylation should usually be avoided. For example, human FGF21 is highly O-glycosylated when prepared recombinantly in yeast.

Claim 1 in US 2002/0068325 relates to a method of producing a heterologous protein in fungi comprising: providing a recipient fungi cell wherein the quality control mechanism in said cell is modified so that incompletely folded heterologous proteins are not degraded in the endoplasmic reticulum; and introducing to said recipient fungi cell a polynucleotide expression construct. According to claim 8 therein, the recipient cell is modified in the mannosyltransferase gene comprising a gene selected from the group consisting of PMT1, PMT2, PMT3, PMT4, PMT5 and PMT6. FGF is not dealt with in said US patent application.

OBJECTS OF THIS INVENTION

The object of this invention is to overcome or ameliorate at least one of the disadvantages of the prior art, or to provide a useful alternative.

Another aspect of this invention relates to the furnishing of a process for effectively preparing FGF21 and analogues thereof.

Another aspect of this invention relates to the furnishing of a recombinant process for preparing FGF21 and analogues thereof having a low degree of O-glycosylation or no O-glycosylation.

Another aspect of this invention relates to the furnishing of a recombinant process in which the degradation of FGF21 and analogues thereof is decreased.

DEFINITIONS

The sequence of the native human FGF21 protein is available from the UNIPROT database with accession no. Q9NSA1. The 209 amino acid precursor protein includes a signal peptide (amino acids 1-28) and a mature protein (amino acids 29-209). The mature human protein is included herein as SEQ ID NO:1 (amino acids 1-181), and the signal peptide as SEQ ID NO:2 (amino acids 1-28).

The term "analogue" as referred to herein in the context of FGF21, i.e., an FGF21 analogue, refers to a polypeptide that is or can be, deduced or derived from native human FGF21, from SEQ ID NO:1 in particular, by modification of the amino acid sequence thereof. Such modification, amendment or change may include substitution, deletion, and/or addition of one or more amino acids. In total, preferably not more than 10, preferred not more than 8, more preferred not more than 6 amino acids are substituted, deleted and/or added. For example, amino acids may be added and/or deleted at the C-terminus, at the N-terminus, or internally in the amino acid sequence. Preferably amino acids are added and/or deleted at the C- and/or N-terminus, more preferably at the N-terminus. Amino acid sequences with C- or N-terminally deleted amino acids may also be referred to as truncated sequences, as is known in the art. Likewise, amino acids added internally in the sequence may be referred to as insertions. The term FGF21 analogue refers to compounds having glucose lowering effect. The glucose lowering effect can be determined as described in WO 2010/0841169, especially example 8 relating to a potency assay for glucose uptake in 3T3-L1 adipocytes. Preferably, said FGF21 analogues have a identity with human FGF21 which is at least 90%, preferably at least 95%. The identity can be determined as described in WO 2010/084169, especially pages 10 & 11.

Herein, the term "PMT" (Protein Mannosyl Transferase) covers enzymes which attach the first mannose on serine or threonine residues in proteins leading to an O-glycosylation mannose tree. However, it is not all serine and threonine residues which are O-glycosylated in a protein. There are at least 6 enzymes in the PMT family (Pmtp1-6). They are grouped in three sub families each group represented by Pmt1 p, Pmt2p or Pmt4p.

Herein, the term "knock out" covers deletion of the open reading frame. The deletion can be either a deletion of the open reading frame or substitution of the open reading frame with a marker. With a 'marker' is meant genes used in classical yeast genetics for deletion of genes and substitution with another gene which activity can be selected for such as TRP1 or KanMX4.

In one embodiment, all the amino acids and amino acid residues dealt with herein are amino acids and amino acid residues which can be coded for by the triplon ("codon") of nucleotides and, hence, the corresponding FGF21 analogues can be prepared recombinantly.

Herein, the term "PMT1" covers Protein-Mannosyl-transferase 1.

Herein, the term "PMT2" covers Protein-Mannosyl-transferase 2.

Herein, the term "PMT4" covers Protein-Mannosyl-transferase 4.

Herein, the term "PEP4" covers protein peptidase A.

Herein, the term "YPS1" covers the YPS1-encoeded aspartic protease yapsin 1 (also called YAP3).

Herein, the term "MKC7" covers glycosyl-phosphatidylinositol-linked aspartyl protease 7.

Herein, the term "TRP1" covers Phosphoribosylanthranilate Isomerase 1.

Herein, the term "kanMX" is used for the gene from Tn903 that confers resistance to the aminoglycosid antibiotic G418 of transformed yeasts.

Herein, the term "marker" is used for genes which gene product activity can be selected for.

BRIEF DESCRIPTION OF THIS INVENTION

Briefly, the present invention is as described in the claims and clauses below.

FGF21 and analogues thereof, e.g., analogues with N-terminal amino acid extensions, can be expressed in *Saccharomyces cerevisiae*. These N-terminal amino acid extensions can consist of up to about 20 amino acids, preferably up to about 15 amino acids and all the amino acids are amino acids which can be coded for by the triplon and prepared recombinantly. In the present invention, this requires strain design in which a strain disrupted in PMT2, PEP4 and YPS1 is created. This strain can be designed using classical techniques relying on homologous recombination allowing specific integration at the respective loci. FGF21 and analogues thereof, e.g., analogues with N-terminal extension or mutations, are coded for on an *S. cerevisiae* expression vector which can be maintained in *S. cerevisiea*. To direct the FGF21 analogue to the secretory pathway a pre-pro sequence including a signal peptide (for example the MFalpha pre-pro leader sequence) may be provided in the recombinant expression vector. This sequence is joined to the DNA encoding the FGF21 analogue in correct reading frame. This signal peptide ensures secretion to the media. Upstream and adjacent to the FGF21 analogue sequence a dibasic amino acid sequence is placed ensuring cleavage of the prepro sequence from the FGF21 analogue before secretion to the media. The cleavage is likely to be caused by Kex2p activity. The FGF21 analogue can be harvested from the media.

Surprisingly, the inventors of the present invention have found that the problem with O-glycosylated FGF21 and analogues thereof when wild type yeast was used was solved by disruption of PMT2 in the expression strain. By deletion of PMT2 from the wild type yeast strain O-glycosylation of FGF21 and analogues thereof was decreased.

DETAILED DESCRIPTION OF THIS INVENTION

Expression of FGF21 in a wild type *S. cerevisiae* yeast strain has proven to be problematic as the FGF21 and analogues thereof are highly O-glycosylated. This invention describes the solution to this problem by expressing FGF21 and analogues thereof in a pmt2 knock out yeast strain. This is a strain where the host PMT2 gene encoding Protein-Mannosyl-transferase 2 (Pmt2p) has been eliminated in a way that is non-reversible.

In wild type yeast, the gene encoding Pmt2p can be disrupted using classical techniques relying on homologous recombination allowing specific replacement of the wildtype PMT2 gene by integration of a deletion allele into the PMT2 locus, using another gene as selectable marker. The selectable marker is a gene, which activity can be selected for such as TRP1, KanMX4 or other markers.

FGF21 and analogues thereof can subsequently be expressed from expression plasmids in this knock out yeast strain resulting in reduced O-glycosylation. It is advantageously to combine the pmt2 knock-out with protease knock-outs in PEP4, YPS1 (YAPS) and MKC7 (YPS2) genes in order to avoid degradation of the expressed protein.

Generally, the DNA is inserted into an expression vector, such as a plasmid, in proper orientation and correct reading frame for expression. The vector is then introduced into the host through standard techniques and, generally, it will be necessary to select for transformed host cells.

Host cells that have been transformed by the recombinant DNA used in this invention are then cultured for a sufficient period of time and under appropriate conditions known to those skilled in the art in view of the teachings disclosed herein to permit the expression and secretion of FGF21 and analogues thereof to be produced according to the method of the invention. The skilled art worker is able to select a culture medium and proper culturing conditions and to recover FGF21 from the medium after the cultivation.

Useful yeast plasmid vectors include the cPOT (Kjeldsen et al. in *Gene* 170: 107-112, 1996) and YEp13, YEp24 (Rose and Broach in *Methods in Enzymol.* 185: 234-279, 1990), and pG plasmids (Schena et al. in *Methods in Enzymol.* 194: 289-398, 1991).

Methods for the transformation of *S. cerevisiae* include the spheroplast transformation, lithium acetate transformation, and electroporation, cf. *Methods in Enzymol.* 194 (1991). Preferably the transformation is as described in the examples herein.

Suitable promoters for *S. cerevisiae* include the MFα1 promoter, galactose inducible promoters such as GAL1, GAL7 and GAL10 promoters, glycolytic enzyme promoters including TPI1 and PGK1 promoters, TRP1 promoter, CYC1 promoter, CUP1 promoter, PHO5 promoter, ADH1 promoter, and HSP promoter. A suitable promoter in the genus *Pichia* is the AOX1 (methanol utilisation) promoter.

The transcription terminal signal is preferably the 3' flanking sequence of a eukaryotic gene which contains proper signal for transcription termination and polyadenylation. Suitable 3' flanking sequences may, e.g., be those of the gene naturally linked to the expression control sequence used, i.e., corresponding to the promoter.

The DNA constructs that are used for providing secretory expression of the desired FGF21 or analogue thereof comprise a DNA sequence that includes a leader sequence linked to the polypeptide by a yeast processing signal. The leader sequence contains a signal peptide ("pre-sequence") for protein translocation across the endoplasmic reticulum and optionally contains an additional sequence ("pro-sequence"), which may or may not be cleaved within yeast cells before the polypeptide is released into the surrounding medium. Useful leaders are the signal peptide of *S. cerevisiae* MFα1p, MFα1*, Yap3p, Bar1p, Hsp150p and *S. kluyveri* MFα signal peptides and prepro-sequences of *S. cerevisiae* MFα1, Yap3p, Prcp, Hsp150p, and *S. kluyveri* MFα and synthetic leader sequences described in WO 92/11378, WO 90/10075 and WO 95/34666.

The DNA sequence encoding the desired FGF21 or analogue thereof may be of genomic or cDNA origin, for instance be obtained by preparing a genomic or cDNA library and screening for DNA sequences coding for all or part of the polypeptide by hybridization using synthetic oligonucleotide probes in accordance with standard techniques (see, for example, Sambrook, J, Fritsch, E F and Maniatis, T in *Molecular Cloning: A Laboratory Manual*, Cold Spring Harbor Laboratory Press, New York, 1989). The DNA sequence encoding FGF21 or an analogue thereof may also be prepared synthetically by established standard methods, e.g. the phosphoamidite method described by Beaucage and Caruthers in *Tetrahedron Letters* 22 (1981), 1859-1869, or the method described by Matthes et al. in *EMBO Journal* 3 (1984), 801-805. The DNA sequence may also be prepared by polymerase chain reaction using specific primers, for instance as described in U.S. Pat. No. 4,683,202 or by Saiki et al. in *Science* 239 (1988), 487-491.

Expression of FGF21 or analogues thereof in this pmt2 knock out strain did not change the expression level in any substantial amount compared with the expression level using a non-pmt2 knock out strain but, as mentioned herein, reduced the O-glycosylation significantly.

In one embodiment of this invention, the expression of FGF21 or analogues thereof is performed using a yeast strain that has knock-outs of YPS1, PEP4 and PMT2.

In one embodiment of this invention, the expression of FGF21 or analogues thereof is performed using a yeast strain that has knock-outs of YPS1, PEP4 and MKC7.

In one embodiment of this invention, the expression of FGF21 or analogues thereof is performed using a yeast strain that has knock-outs of YPS1, PEP4, MKC7 and of PMT2.

In one embodiment of this invention, the FGF21 analogue contains Ala or His in position 17 and/or 36. Hereby, the degree of degradation is lowered.

If the task is to prepare human FGF21, the process of this invention is to be performed at conditions at which the ratio between O-glycosylated FGF21 and non-O-glycosylated FGF21 obtained is below about 20%, preferably below about 10%, more preferred below about 5% and even more preferred below about 2% (weight/weight). Similarly, this applies if the task is to prepare an analogue of FGF21.

PREFERRED FEATURES OF THIS INVENTION

To sum up and supplement the above statements, the features of this invention are as follows:
1. A process for recombinant expression of human FGF21 and analogues thereof in yeast wherein the yeast used is a pmt2 knock out strain.
2. A process according to clause 1, wherein an FGF21 analogue with an N-terminal extension is prepared.
3. The process according to clause 1, wherein the yeast used is *Saccharomyces cerevisae*.
4. The process according to clause 1 or 2, wherein the yeast used is a pep4 knock out strain.
5. The process according to any one of the preceding clauses, wherein the yeast used is an yps1 knock out strain.
6. The process according to any one of the preceding clauses, wherein the yeast used is an mkc7 knock out strain.
7. The process according to any one of the preceding clauses, wherein the yeast is cultivated at conditions at which the exogenous DNA sequence is expressed and the desired FGF21 or an analogue thereof is recovered.
8. The process according to any one of the preceding clauses, wherein said FGF21 is secreted into the culture medium.
9. The process according to any one of the preceding clauses, wherein the knock out pmt2 yeast strain is prepared using the TRP1 marker or KanMX4 marker, preferably the TRP1 marker.
10. The process according to any one of the preceding clauses, wherein the ratio between the resulting O-glycosylated FGF21 or a derivative thereof, on one hand, and the resulting non-O-glycosylated FGF21 or an analogue thereof, on the other hand, is below about 20%, preferably below about 10%, more preferred below about 5% and even more preferred below about 2% (weight/weight).
11. A process according to any one of the preceding clauses, wherein the FGF21 analogue prepared has been mutated at position R17 and/or R36.
12. A process according to any one of the preceding clauses, wherein the FGF21 analogue prepared has been mutated at position R17 and/or R36, preferably to obtain less degradation in yeast expression.
13. Human FGF21 prepared by a process according to any one of the preceding processes.
14. Any novel feature or combination of features described herein, especially features described in a clause or in a claim.

Combining one or more of the clauses and embodiments described herein, optionally also with one or more of the claims below, results in further embodiments and the present invention relates to all possible combinations of said clauses, embodiments and claims.

The following examples are offered by way of illustration, not by limitation.

EXAMPLE

General Procedures

All expressions plasmids are of the cPOT type, similar to those described in EP 171,142. These are 2μ-based expression vectors characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator. These sequences are similar to the corresponding sequences in plasmid pKFN1003 (described in WO 90/10075). In order to facilitate cloning of different fusion proteins the DNA sequence encoding the MFα1 pre-pro leader has been changed to incorporate a NcoI site and is called the MFα1* pre-pro leader. Thus the NcoI-XbaI fragment is simply replaced by an NcoI-XbaI fragment encoding the FGF21 construct or that of an analogue thereof. Such NcoI-XbaI fragments may be synthesized using synthetic oligonucleotides and PCR according to standard techniques. In addition to the alpha-leader other leaders can be used.

Yeast transformants and derivatives thereof were prepared by transformation of the host *S. cerevisiae* strains. The yeast strains were grown in liquid YPGGE (1% Bacto yeast extract, 2% Bacto peptone, 2% galactose, 2% glycerol, 1% ethanol) to an O.D. at 600 nm of 0.6. 100 ml of culture were harvested by centrifugation, washed with 10 ml of water, recentrifuged and resuspended in 10 ml of a solution containing 1.0 M sorbitol, 25 mM Na$_2$EDTA pH 8.0 and 6.7 mg/ml dithiothreitol. The suspension was incubated at 30° C. for 15 minutes, centrifuged and the cells resuspended in 10 ml of a solution containing 1.0 M sorbitol, 10 mM Na$_2$EDTA, 0.1 M sodium citrate, pH 5.8, and 2 mg Glucanex 200G (Novozyms). The suspension was incubated at 30° C. for 30 minutes, the cells collected by centrifugation, washed in 10 ml of 1.2 M sorbitol and 10 ml of CAS (1.0 M sorbitol, 10 mM CaCl$_2$, 10 mM Tris HCl pH 7.5) and resuspended in 2 ml of CAS. For transformation, 1 ml of CAS-suspended cells was mixed with approximately 0.1 mg of plasmid DNA and left at room temperature for 15 minutes. 1 ml of (20% polyethylene glycol 4000, 10 mM CaCl$_2$, 10 mM Tris HCl, pH 7.5) was added and the mixture left for a further 30 minutes at room temperature. The mixture was centrifuged and the pellet resuspended in 0.1 ml of SOS (1.2 M sorbitol, 33% v/v YPD, 6.7 mM CaCl$_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) in *Methods in Yeast Genetics*, Cold Spring Harbor Laboratory) containing 1.2 M sorbitol plus 2.5% agar at 52° C. was added and the suspension poured on top of plates containing the same agar-solidified, sorbitol containing medium.

Example 1 pmt1::KanMX4, pmt2::KanMX4 and pmt4::KanMX4 Gene Disruptions in ME1487

A yeast strain BY4741-pmt2 with the PMT2 gene deleted and the genotype Mat a his3D1 leu2D0 lys2D0 ura3D0 yal023c::kanMX4, was purchased from the Euroscarf deletion strain collection. In this yeast strain, the DNA fragment encoding the PMT2 open reading frame has been replaced with the KanMX4 dominant selectable marker, conferring resistance to the antibiotic G418/geneticin (Wach et al. Yeast 10 (1994)1793-1808.

Genomic DNA was isolated from BY4741 and used as template in a standard PCR reaction with synthetic oligonucleotides oILLa-0056: CCGTTTCGTGTACTGTTTA and oILLa-0079: GGCTAAAGGGTTCAAGAAAT in order to amplify a synthetic DNA fragment containing the Δpmt2::KanMX4 deletion allele cassette. This DNA fragment was used directly for transformation of ME1487: MATα, tpi::LEU2 pep4-3 leu2 ura3 yps1::URA3 (Egel-Mitani et al. *Enzyme and Microbial Technology* 26 (2000), 671-677) containing the cPOT plasmid expressing FGF21. Transformation of yeast was done by the lithium acetate/single-stranded carrier DNA/polyethylene glycol method (*Methods in Enzymology:* 350, 87-96). After transformation, the yeast cells were plated on YEPD (1% yeast extract, 2% peptone, 2% dextrose) agar and incubated overnight at 30° C. followed by replica-plating onto selective YEPD agar+200 mg/L G418. Yeast colonies appearing after 3 days further incubation at 30° C. were isolated and characterized by PCR which verified the correct integration of pmt2::KanMX4 allele into the PMT2 locus and thus confirmed the replacement of the wild type allele with the deletion allele. The genotype of the resulting strain, yDNP-255, was MATα, tpi1::LEU2 pep4-3 leu2 ura3 yps1::URA3 pmt2::kanMX4. yDPN-255 contained the cPOT plasmid expressing FGF21.

Similarly, the locus PMT1 and PMT4 were disrupted creating the strains: yDNP-257: MATα, tpi1::LEU2 pep4-3 leu2 ura3 yps1::URA3 pmt1::kanMX4 and yDNP-260: MATα, tpi1::LEU2 pep4-3 leu2 ura3 yps1::URA3 pmt4::kanMX4. Both containing the cPOT plasmid expressing FGF21.

Example 2 pmt2:: TRP1-FA Gene Disruption in NNY574

The auxotrophic marker, the trp1-FA deletion, was introduced into a *S. cerevisiae* bagground strain to facilitate classical one-step knock out of relevant genes, as described by Horecka and Jigami (Horecka and Jigami *Yeast* 15 (1999) 1769-1774; The trp1-FA designer deletion for PCR-based gene functional analysis in *Saccharomyces cerevisiae. Yeast* 15, 1769-1774). The fragment deleted from the TRP1 locus corresponded exactly to a cassette termed TRP1-FA carried in many yeast vectors and was composed of 141 by from the 5'-untranslated region followed by the TRP1 open reading frame followed by 50 by from the 3'-untranslated region. In order to introduce the trp1-FA deletion, the strain of interest was transformed with a PCR fragment containing the fused 5'- and 3'-untranslated regions from further upstream and downstream the TRP1-FA region for a classical one-step deletion of TRP1-FA. Deletion of the TRP1-FA region was verified by PCR. This strain had then PMT2 gene deleted by transformation with a DNA fragment consisting of the TRP1-FA cassette flanked by the pmt2 5'-untranslated region and the pmt2 3'-untranslated region, followed by selection for the TRP1-FA marker phenotype. Recombination of the pmt2::TRP1-FA allele into the PMT2 locus resulted in replacement of the wildtype PMT2 gene with pmt2::TRP1-FA allele. Isolated yeast cells were characterized by classical yeast genetic methods. Correct integration was confirmed by PCR.

Example 3

Western blot analysis was used to determine the effect of pmt1, pmt2 and PMpmt4 knock out on the expression of FGF21 compared to a wild type strain. Samples of media from the cultivated yeast strains secreting FGF21 were run on 4-12% BisTris SDS page in Mes-SDS buffer. The proteins in the gel were transferred to nitrocellulose and immunostained with polyclonal FGF21 antibody goat FGF21 (Santa Cruz sc-16842), and secondary donkey anti goat IgG-HRP (Santa Cruz sc-2020). For detection the chemifluorescence detection method was used. The result was that in the wild trype strain FGF21 migrated as a double band. When PMT4 was deleted it had no effect. When PMT1 was deleted it has some effect but when PMT2 was deleted FGF21 migrated as a single band and O-glycosylation was significantly decreased.

Example 4

Deletion of the PMT2 gene from the host can be used for secretory expression of FGF21 analogues in *S. cerevisiae*. In the FGF21 analogues, amino acids can be amended or changed, substituted, deleted, and/or one or more amino acids can be added or combinations thereof. When expressing the FGF21 analogues in the *S. cerevisiae* host with deletion of the PMT2 gene, O-glycosylation is decreased significantly. This can be observed by Western blot analysis of the growth medium from cultivation of the *S. cerevisiae* strain secreting FGF21 or FGF21 analogues, as described in Example 3. FGF21 and analogues thereof migrate as a double band when secreted from a wild type strain. This is changed when expression is from a pmt2 knock out *S. cerevisae* host. Then, human FGF21 and the FGF21 analogue will migrate as a single band.

For FGF21 analogue expression the desired sequence was inserted in the cPot expression vector and transformed into the pmt2 knock out strain described in Example 3 above. FGF21 analogues comprising the following mutations, insertions and/or extensions were made:
1) −1G, K56R, K59R, K69R, K122R
2) −5G, −4S, −3G, −2S, −1G, K56R, K59R, K69R, D102E, N121Q, K122R, M168L
3) −14E, −13E, −12A, −11E, −10A, −9G, −8G, −7A, −6G, −5G, −4S, −3G, −2G, −1S, K56R, K59R, K69R, K122R 4) −15E, −14E, −13S, −12A, −11A, −10S, −9G, −8A, −7A, −6A, −5G, −4S, −3A, −2A, −1A, K56R, K59R, K69R, K122R)
5) K56R, K59R, K69R, K122R)
6) −5G, −4S, −3G, −2S, −1G, K56R, K59R, K69R, K122R)
7) −1G The supernatants from yeast cultures secreting the above compounds were analysis on Western blot analysis as described in Example 3. It was observed that only a single band visualized with polyclonal FGF21 antibody appeared on the Western blot and not a double band as FGF21 in a wild type *S. cerevisiae* strain confirming the effect of deletion of pmt2 in the expression strain.

The nomenclature used for the above compounds is as described in WO 2010/084169, especially at pages 6-11.

Example 5

LC-MS analysis using a LC/MSD TOF instrument (Agilent) is used to determine the molecular mass of secreted peptides in yeast supernatans according to the settings recommended by the manufacturer. Deconvolution of the TIC chromatogram is done using the accompanying software. The abundances of full-length and O-glycosylated species is obtained from the deconvoluted spectrum and used for estimation of the percentage of full-length peptide vs the pool of full-length and O-glycosylated FGF21.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

The citation and incorporation of patent documents herein is done for convenience only and does not reflect any view of the validity, patentability, and/or enforceability of such patent documents. The mentioning herein of references is no admission that they constitute prior art.

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Herein, the word "comprise" is to be interpreted broadly meaning "include", "contain" or "comprehend" (vide, EPO guidelines C, III, 4.13).

This invention includes all modifications and equivalents of the subject matter recited in the claims and clauses appended hereto as permitted by applicable law.

What is claimed is:

1. A process for preparing FGF21 having a sequence of SEQ ID NO:1 and analogues thereof, comprising the steps of:
   a. introducing an expression vector comprising a DNA molecule encoding FGF21 or analogues thereof into a *Saccharomyces cerevisiae* yeast strain having a ymt2 knockout;
   b. culturing said yeast under conditions for expressing and secreting FGF21 or analogues thereof.

2. The process according to claim 1, wherein an FGF21 analogue with an N-terminal extension is prepared.

3. The process according to claim 1, wherein the yeast strain further having pep4 knock out.

4. The process according to claim 1, wherein the yeast strain further having yps1 knock out.

5. The process according to claim 1, wherein the yeast strain further having mkc7 knock out.

6. The process according to claim 1, further comprising recovering FGF21 or analogues thereof.

7. The process according to claim 1, wherein said FGF21 is secreted into a culture medium.

8. The process according to claim 1, wherein the knock out pmt2 yeast strain is prepared using TRP1 marker or KanMX4 marker.

9. The process according to claim 8, wherein the knockout pmt2 yeast strain is prepared using TRP1 marker.

10. The process according to claim 1, wherein the FGF21 or analogues thereof is prepared with a ratio between O-glycosylated and non-O-glycosylated below about 20% (weight/weight).

11. The process according to claim 10, wherein the ratio is below about 10% (weight/weight).

12. The process according to claim 10, wherein the ratio is below about 5% (weight/weight).

13. The process according to claim 10, wherein the ratio is below about 2% (weight/weight).

14. The process according to claim 1 wherein the FGF21 analogue prepared has been mutated at position R17 and/or R36, wherein the position corresponds to the amino acid position of SEQ ID NO:1.

15. The process according to claim 1, wherein said yeast is a yeast strain further having knockouts of yps1 and pep4.

16. The process according to claim 1, wherein said yeast is a yeast strain further having knockouts of yps1, pep4, and mkc7.

* * * * *

UNITED STATES PATENT AND TRADEMARK OFFICE
CERTIFICATE OF CORRECTION

PATENT NO.        : 9,120,871 B2
APPLICATION NO.   : 13/522804
DATED             : September 1, 2015
INVENTOR(S)       : Rita Slaaby et al.

Page 1 of 1

It is certified that error appears in the above-identified patent and that said Letters Patent is hereby corrected as shown below:

In the claims,

At column 11, claim number 1, line number 29, please replace "…ymt2 knockout…" with "…pmtz knockout…"

Signed and Sealed this
Nineteenth Day of July, 2016

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 181
<212> TYPE: PRT
<213> ORGANISM: Homo sapiens
<220> FEATURE:
<221> NAME/KEY: mat_peptide
<222> LOCATION: (1)..(181)
<220> FEATURE:
<221> NAME/KEY: DISULFID
<222> LOCATION: (75)..(93)

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
```

```
145                 150                 155                 160
Gly Ser Ser Asp Pro Leu Ser Met Val Gly Pro Ser Gln Gly Arg Ser
                165                 170                 175
Pro Ser Tyr Ala Ser
            180

<210> SEQ ID NO 2
<211> LENGTH: 28
<212> TYPE: PRT
<213> ORGANISM: Homo sapiens
<220> FEATURE:
<221> NAME/KEY: SIGNAL
<222> LOCATION: (1)..(28)

<400> SEQUENCE: 2

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala
                20                  25
```